US00PP17190P2

(12) United States Plant Patent
Korlipara

(10) Patent No.: US PP17,190 P2
(45) Date of Patent: Nov. 7, 2006

(54) ***VERBASCUM* PLANT NAMED 'SUNSHINE SPIRES'**

(50) Latin Name: *Verbascum hybrid*
Varietal Denomination: Sunshine Spires

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 38 days.

(21) Appl. No.: 11/155,039

(22) Filed: Jun. 16, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—Klarquist Sparkman, LLP

(57) ABSTRACT

A new and distinct *Verbascum* plant characterized by numerous bright yellow flowers on numerous upright flowering stems, a compact habit, and excellent vigor.

1 Drawing Sheet

Botanical classification: *Verbascum* hybrid ((*V. phoeniceum*×*dumulosum*)×*V.* sp. 'Electric Yellow').

Variety denomination: 'Sunshine Spires'.

Cross reference to: co-pending application for *Verbascum* 'Sierra Sunset' (U.S. Plant patent application Ser. No. 11/154,433, filed Jun. 15, 2005).

The present invention relates to a new and distinct cultivar of *Verbascum* hybrid, and given the cultivar name 'Sunshine Spires'. *Verbascum* is in the family Scrophulariaceae.

This new cultivar originated from a cross between *Verbascum* 'Jackie' (an unpatented plant) as the seed parent and *Verbascum* sp. 'Electric Yellow' (an unpatented plant) as the pollen parent. *Verbascum* 'Jackie' is a cross between *Verbascum phoeniceum* and *Verbascum dumulosum.*

This new *Verbascum* hybrid is unique in its bright yellow colored flowers combined with its *Verbascum* 'Jackie'-like compact habit and short, multiple flowering stems.

This plant is characterized by the following:

1. Large bright yellow flowers.
2. Numerous upright, branching flowering stems.
3. Compact habit.
4. Excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows the whole plant of a one year old *Verbascum* 'Sunshine Spires' grown in the trial field in bloom in summer.

DETAILED PLANT DESCRIPTION

The following is a detailed description of the new *Verbascum* selection based on observations of one-year-old specimens grown in the ground in full sun under typical outdoor conditions Canby is Zone 8 on the USDA Hardiness map. Temperatures range from a high of 95 degrees F. in August to 32 degrees F. in January. Normal rainfall in Canby is 42.8 inches per year in the trial fields in Canby, Oreg. The color descriptions are all based on The Royal Horticultural Society Colour Chart.

Plant:

*Type.*—Herbaceous perennial.
*Form.*—Clumping basal rosette.
*Hardiness.*—U.S.D.A. Hardiness Zones 6–9.
*Size.*—14 cm tall and 42 cm wide, not including inflorescence.
*Vigor.*—Excellent.
*Roots.*—Fibrous, with many downward growing and few laterals, ivory in color, Yellow White 158D. Roots develop slowly from cuttings from the crown.

Leaf:

*Type.*—Simple.
*Arrangement.*—Basal.
*Shape.*—Ovate.
*Blade size.*—Grows to 23 cm long and 14 cm wide.
*Venation.*—Pinnate.
*Margins.*—Irregularly crenate overall, slightly undulate.
*Apex.*—Acute.
*Base.*—Cuneate.
*Texture.*—Leathery, fuzzy.
*Surface.*—Stellate pubescent on both sides.
*Petiole.*—Length — Grows to 3 cm. Width — Grows to 14 mm. Surface — Stellate pubescent. Color — Yellow Green 145C.
*Leaf color.*—Topside — Green 147B with lighter main vein, Yellow Green 145B. Bottom side — Yellow Green 147B.

Inflorescence:

*Type.*—Panicle.
*Total panicle size.*—15 cm wide and 47 cm high (where flowers are).
*Number of panicles per plant.*—5.

*Cauline leaves.*—In 1 cm internodes, 3 to 13 cm long and 3 to 8 cm wide, sessile, ovate, with tips acute to acuminate, margins crenate.

*Flower number.*—Count of 220 flowers on one panicle.

*Peduncle.*—Height — Grows to 72 cm. Diameter — 15 mm near base. Surface — Stellate pubescent. Color — Yellow Green 145B to 146D.

*Pedicel.*—Length — Grows to 10 mm. Surface — Stellate pubescent. Color — Yellow Green 144D.

*Bloom time.*—May to August in Canby, Oreg.

Flower bud:

*Size.*—11 mm wide and 10 mm deep.

*Description.*—Pentagonal cushion.

*Surface.*—Stellate pubescent.

*Color.*—Greyed Orange 162A with tints of Greyed Orange 167A.

Flower:

*Type.*—Perfect. Complete. Irregular.

*Shape.*—Rotate, irregular, short tubular.

*Size.*—3 cm wide and 1 cm deep including stamens. Color — Yellow 9A on both sides. The center of the inside of the corolla is eyed dull purple, Greyed Purple 186A.

*Corolla.*—Lobe number — 5. Description — Lobes slightly undulate, entire, apex obtuse. Size — 3 cm wide and 1 cm deep. Surface — Backs stellate pubescent.

*Calyx.*—Sepal number — 5. Size — 10 mm wide and 7 mm deep. Surface — Stellate pubescent on both sides. Color — Yellow Green 146B on both sides.

*Stamens.*—Number — 5. Filaments — 7 mm long, Yellow 9A on lower two stamens and bearded Purple 77A, upper three stamens Orange 17C and heavily bearded Yellow 9D. Anthers — Kidney shaped. Orange 24A. Pollen — Orange 28A.

*Style.*—12 mm long, Yellow Green 144A.

*Stigma.*—Yellow Green 144A.

*Fragrance.*—None.

Fertility: Sterile, no fruit or seed produced.

Disease and pests: *Verbascum* are susceptible to fungal leaf spots and root rots. They need good drainage. Caterpillars may be a problem.

COMPARISONS

Compared to *Verbascum* 'Jackie' (unpatented), the seed parent, *Verbascum* 'Sunshine Spires' is similar in its branching and free flowering. The greatest difference is the flower color. *V.* 'Jackie' is described as having copper colored buds, which open to pale peach colored flowers and lavender stamens. The new cultivar has yellow orange buds that open to bright yellow flowers. The habit of this new cultivar is larger than *Verbascum* 'Jackie'.

Compared to *Verbascum* 'Electric Yellow' (unpatented), the pollen parent, *Verbascum* 'Sunshine Spires' has smaller flowers, much more branching, and is much shorter.

Compared to *Verbascum* 'Honey Dijon' (U.S. patent application Ser. No. 11/153,519), *Verbascum* 'Sunshine Spires' has bright yellow flowers rather than gold flowers, and has taller flowering stems.

I claim:

1. A new and distinct *Verbascum* plant as herein illustrated and described.

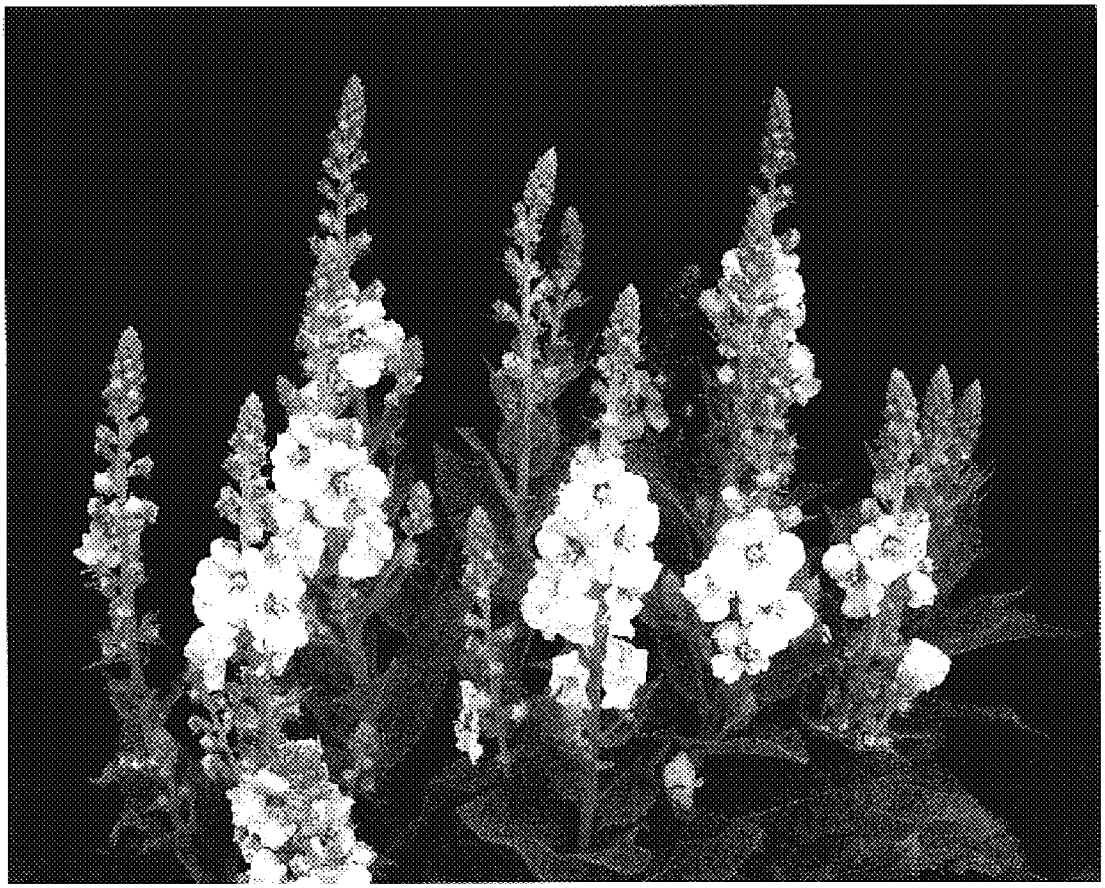

* * * * *